US005082863A

United States Patent [19]

Apelian et al.

[11] Patent Number: 5,082,863

[45] Date of Patent: Jan. 21, 1992

[54] PHARMACEUTICAL COMPOSITION OF FLORFENICOL

[75] Inventors: Henry M. Apelian, Clark; David Coffin-Beach, Kendall Park; Abu S. Huq, Plainsboro, all of N.J.

[73] Assignee: Schering Corporation, Kenilworth, N.J.

[21] Appl. No.: 574,430

[22] Filed: Aug. 29, 1990

[51] Int. Cl.[5] .................... A61K 31/00
[52] U.S. Cl. .................... 514/618; 514/947
[58] Field of Search .................... 514/618, 947

[56] References Cited

U.S. PATENT DOCUMENTS 4,423,040 12/1983 Rajadhyaksha .................... 514/947

*Primary Examiner*—S. Friedman
*Attorney, Agent, or Firm*—John J. Maitner; Eric S. Dicker

[57] ABSTRACT

An injectable pharmaceutical composition for veterinary use is disclosed comprising Florfenicol, N-methyl-2-pyrrolidone, polyethylene glycol and a viscosity reducing agent. The composition is chemically and physically stable, exhibits constant blood levels and does not product undesirable side effects.

5 Claims, 1 Drawing Sheet

SERUM FLORFENICOL LEVELS IN CALVES
AFTER A SINGLE I.M. 20 MG/KG DOSE

PHARMACEUTICAL COMPOSITION OF FLORFENICOL

BACKGROUND OF THE INVENTION

This invention relates to pharmaceutical compositions containing florfenicol as the active ingredient, and particularly to injectable compositions having a high concentration of florfenicol.

Florfenicol [D-(threo)-1-p-methylsulfonyl phenyl-2-dichloroacetamido-3-fluoro-l-propanol] is a known antibacterial agent and is useful for veterinary purposes. When treating a large animal, it is sometimes desirable to administer a composition having a high concentration of florfenicol. The large amount of florfenicol thus administered should then preferably exhibit constant blood levels and be active for a prolonged period of time.

Florfenicol has low solubility in water, about 1.3 mg/ml, and the preparation of a concentrated aqueous injectable solution is not practicable due to the large volume required to administer a therapeutic dose.

Florfenicol also exhibits low solubility in many pharmaceutically acceptable organic solvents such as 1,2-propanediol, glycerin, and benzyl alcohol.

Florfenicol is generally soluble in aprotic polar solvents, such as N-methyl-2-pyrrolidone or 2-pyrrolidone; however, concentration of these solvents at levels greater than 30% was found to cause injection site irritation and tissue damage upon intramuscular administration.

SUMMARY OF INVENTION

It has been found that stable injectable compositions of florfenicol can be provided by means of a novel composition comprising:

10 to 50% by weight of Florfenicol;

10 to 65% by weight of a pyrrolidone solvent;

5 to 15 by weight of a viscosity reducing agent; and 5 to 40% by weight of polyethylene glycol.

The novel compositions provide constant blood levels over a prolonged period of time and exhibit excellent physical and chemical stability.

DETAILED DESCRIPTION OF THE INVENTION

Figure 1:
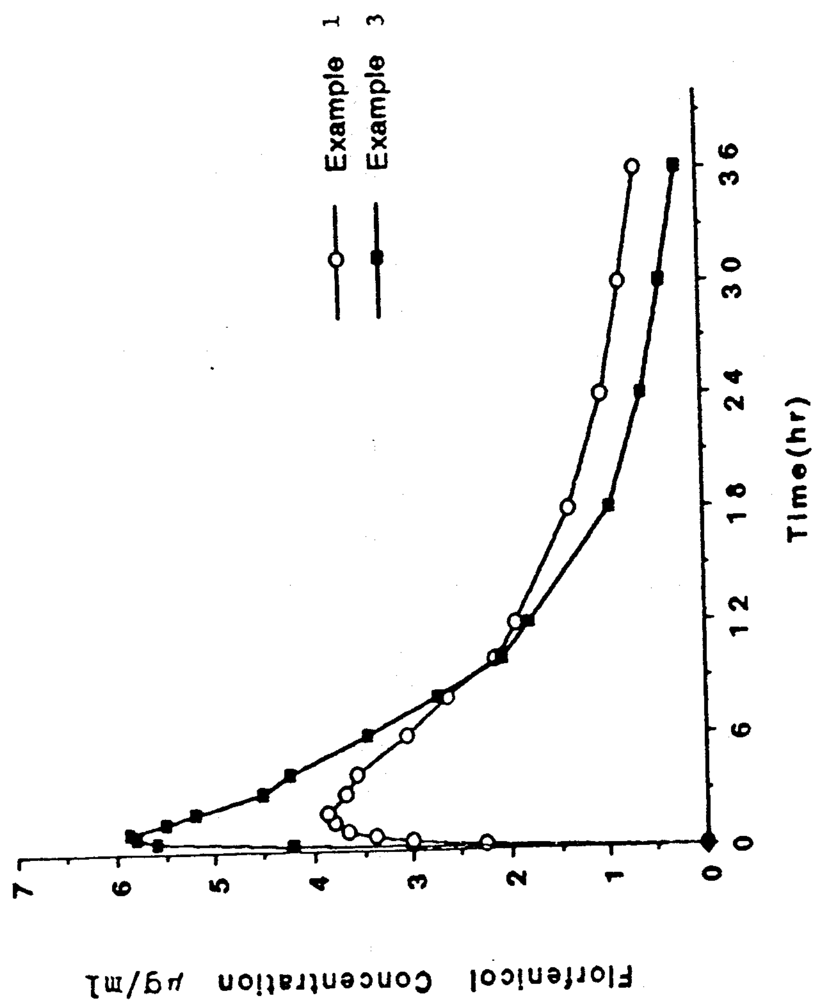
FIG. 1 illustrates serum florfenicol levels in calves after single intramuscular 20 mg/kg dose.

Florfenicol exhibits antibacterial activity and is useful in veterinary medicine (Merck Index, 11th Edition, No. 4042). U.S. Pat. No. 4,235,892, describes the compound and processes for making said compound; this patent is incorporated herein by reference.

According to the present invention, a novel composition has been prepared which provides relatively high concentrations of florfenicol in a unique organic solvent system of a pyrrolidone solvent such as 2-pyrrolidone, N-methyl-2-pyrrolidone; polyethylene glycol, and a viscosity reducing agent.

Compositions according to the present invention may comprise from 10 to 50% by weight of florfenicol, and preferably from 20 to 40% by weight.

The pyrrolidione solvents that can be utilized in this invention include 2-pyrrolidone and N-methyl-2-pyrrolidone. The preferred solvent is N-methyl-2-pyrrolidone. The amount of pyrrolidone solvent in the compositions of the present invention may comprise from 10 to 65% by weight of the total composition. Compositions containing above 30% by weight N-methyl-2-pyrrolidone solvent may cause injection site irritation and tissue damage upon intramuscular injection in cattle.

The polyethylene glycols which are used in the compositions of the present invention include those having an average molecular weight of from 200–400. The preferred polyethylene glycol has an average molecular weight of about 300 and is also referred to as PEG 300. The amount of polyethylene glycol present in the compositions of the present invention is from 5 to 45% by weight, and preferably from 30 to 40% by weight.

Due to the high solids content of florfenicol in the compositions of the present invention, a viscosity reducing agent is required to provide a product with workable syringeability. Examples of viscosity reducing agents useful in the present invention include: ethanol and propylene glycol. The preferred viscosity reducing agent is propylene glycol. The amount of viscosity reducing agent employed in the compositions of the present invention is from 5 to 15% by weight of the composition; preferably 10 to 15% by weight.

The compositions of the present invention are readily prepared by mixing the pyrrolidone solvent and the viscosity reducing agent with approximately 90% of the polyethylene glycol component. The florfenicol is dissolved in the solution and the volume is adjusted with the remaining polyethylene glycol. The resulting clear solution is sterilized by filtration.

The compositions of the present invention exhibit desirable properties which are useful for administration of relatively high concentrations of florfenicol. The compositions have desirable viscosity characteristics which allows for good syringeability over a wide temperature range and ease of processing, such as good flow rate through sterilizing filter membranes. The compositions are physically and chemically stable, for example, the compositions are stable and maintain specification for at least two years when stored at temperatures between 2° C. and 30° C. The compositions provide therapeutic blood levels over a prolonged period of time and also exhibit acceptable tissue toleration.

The following examples describe in detail the invention. It will be apparent to those skilled in the art that modifications, may be practiced without departing from the purpose and intent of this disclosure.

EXAMPLE 1

An injectable solution is prepared from the following:

| Ingredients | Weight/ml |
|---|---|
| Florfenicol | 300 mg |
| N-methyl-2-pyrrolidone | 250 mg |
| Propylene glycol | 150 mg |
| Polyethylene glycol 300 | Qs. ad. 1 ml. |

The solution is prepared according to the following procedure: The N-methyl-2-pyrrolidone, propylene glycol and approximately 90% of the polyethylene glycol 300 required are mixed well and then florfenicol dissolved in the mix. The volume is adjusted with the PEG 300 remaining and the clear solution is sterilized by filtration.

Intramuscular administration of the above noted formulation to cattle at a single dose of 20 mg/kg of florfenicol resulted in the following serum levels:

Concentration (max): 3.86 μg/ml
Concentration (12 hours): 1.94 μg/ml
Concentration (24 hours): 1.03 μg/ml

EXAMPLE 2

An injectable solution is prepared from the following:

| Ingredients | Weight/ml |
|---|---|
| Florfenicol | 300 mg |
| N-methyl-2-pyrrolidone | 250 mg |
| Ethanol | 100 mg |
| Polyethylene glycol 300 | qs to ml |

The solution is prepared according to the following procedure: The N-methyl-2-pyrrolidone, ethanol and approximately 90% of the polyethylene glycol 300 required, are mixed well and then florfenicol dissolved in the mix. The volume is adjusted with the PEG 300 remaining and the clear solution is sterilized by filtration.

EXAMPLE 3

An injectable solution is prepared from the following:

| Ingredients | Weight/ml |
|---|---|
| Florfenicol | 300 mg |
| N-methyl-2-pyrrolidone | 350 mg |
| Propylene glycol | 150 mg |
| Polyethylene glycol 300 | Qs. ad. 1 ml. |

The solution is prepared according to the following procedure described in Example 1.

Intramuscular administration of the above noted formulation to cattle at a single dose of 20 mg/kg of florfenicol resulted in the following serum levels:

Concentration (max): 5.80 μg/ml
Concentration (12 hours): 1.80 μg/ml
Concentration (24 hours): 0.60 μg/ml

EXAMPLE 4

An injectable solution is prepared from the following:

| Ingredients | Weight/ml |
|---|---|
| Florfenicol | 300 mg |
| N-methyl-2-pyrrolidone | 350 mg |
| Ethanol | 100 mg |
| Polyethylene glycol 300 | Qs. ad. 1 ml |

The solution is prepared according to the following procedure described in Example 2.

What is claimed is:

1. An injectable pharmaceutical composition for veterinary use comprising:

10 to 50% by weight of florfenicol;

10 to 65% by weight of a pyrrolidone solvent selected from the group consisting of 2-pyrrolidone and N-methyl-2-pyrrolidone;

5 to 15% by weight of a viscosity reducing agent selected from the group consisting of ethanol and propylene glycol:

5 to 40% by weight of polyethylene glycol having an average molecular weight between 200 and 400.

2. The pharmaceutical composition of claim 1 wherein the pyrrolidone solvent is N-methyl-2-pyrrolidone.

3. The pharmaceutical composition of claim 1 wherein the polyethylene glycol has an average molecular weight of 300.

4. The pharmaceutical composition of claim 1 wherein the viscosity reducing agent is propylene glycol.

5. The pharmaceutical composition of claim 1 comprising:

| Weight/ml | Ingredient |
|---|---|
| 300 mg | Florfenicol |
| 250 mg | N-methyl-2-pyrrolidone |
| 150 mg | Propylene glycol |
| Qs. ad. 1 ml | Polyethylene glycol 300 |

* * * * *